United States Patent [19]

Pye et al.

[11] 4,165,258

[45] Aug. 21, 1979

[54] PLASMINOGEN ACTIVATING ENZYME-SPECIFIC COMPETITIVE INHIBITOR

[75] Inventors: E. Kendall Pye, Media; Thomas Maciag; Michael K. Weibel, both of Philadelphia; Melicote R. Iyengar, Gladwyne, all of Pa.

[73] Assignee: University of Pennsylvania, Philadelphia, Pa.

[21] Appl. No.: 620,792

[22] Filed: Oct. 8, 1975

[51] Int. Cl.$^2$ .................... C07G 7/02; C07C 103/20; C07C 103/28

[52] U.S. Cl. ................... 435/215; 435/212; 435/815; 260/502.6; 260/544 S; 260/558 S; 260/556 AR; 536/54

[58] Field of Search .............. 195/66, 66 B, 63, 68, 195/DIG. 11, 99; 260/470, 516, 518 R, 558 S, 471 R, 556 AR, 544 S, 502.6

[56] References Cited

U.S. PATENT DOCUMENTS

| | | | |
|---|---|---|---|
| 3,027,405 | 3/1962 | Spivack et al. | 260/518 R X |
| 3,732,146 | 5/1973 | Heimburger | 195/66 B |
| 3,801,633 | 4/1974 | Toyoshima et al. | 260/518 R |
| 3,834,990 | 9/1974 | Werle et al. | 195/68 |
| 3,845,097 | 10/1974 | Toyoshima et al. | 260/516 X |
| 3,852,338 | 12/1974 | Kaiser et al. | 260/516 X |

OTHER PUBLICATIONS

Maciag et al., Urokinase, Methods in Enzymology, vol. XXXIV 12/1974 (pp. 451–459).

Maciag et al., Purification of Urokinase by Affinity Chromatography, Enzyme Engineering, vol. 2, Plenum Press, N.Y. 10/1/74, (pp. 55–62).

*Primary Examiner*—David M. Naff
*Attorney, Agent, or Firm*—Holman & Stern

[57] ABSTRACT

A novel plasminogen activating enzyme-specific competitive inhibitor is disclosed consisting of an amino-terminated α-N-substituted aminocarboxylic acid, such as α-N-benzylsulfonyl-p-aminophenylalanine, or the acid derivatives thereof. The competitive inhibitor ligand, when covalently coupled to the surface of a water-insoluble solid support material through a spacer chain of at least 4 carbon atoms, is useful as a biospecific extracting agent for use in affinity chromatography of plasminogen activating enzymes, such as urokinase, cytokinase, and the like, from crude aqueous preparations thereof, such as mammalian urine, mammalian body tissue preparations, mammalian plasma and spent tissue culture growth medium.

28 Claims, No Drawings

PLASMINOGEN ACTIVATING ENZYME-SPECIFIC COMPETITIVE INHIBITOR

BACKGROUND OF THE INVENTION

This invention relates generally to enzyme extraction and purification and, more particularly, to the extraction and purification of plasminogen activating enzymes by affinity chromatography.

Plasminogen activating enzymes, such as urokinase, cytokinase, and the like, catalyze the conversion of plasminogen to plasmin, an enzyme which is capable of lysing fibrin clots. The plasminogen activating enzymes have been shown to have therapeutic value when injected in humans as an effective thrombolytic agent for dissolving blood clots. Various biological sources are known to contain plasminogen activating enzymes in low concentrations. For example, urokinase is a plasminogen activating enzyme present in mammalian urine, and cytokinase is a plasminogen activating enzyme present in mammalian body tissue. Other plasminogen activating enzymes are present in plasma and in spent tissue culture growth medium.

Various attempts have previously been made to extract and purify the plasminogen activating enzymes from their biological sources. These attempts have depended for the most part on inefficient, expensive and time-consuming multi-step procedures involving a combination of several different extraction and purification techniques, including precipitation, centrifugation, dialysis, ion exchange chromatography and gel filtration chromatography.

The potentially simpler and more efficient extraction and purification technique of affinity chromatography, which has been used in recent years in the extraction and purification of some other types of enzymes, has not met with any appreciable success when applied to the extraction and purification of plasminogen activating enzymes. In affinity chromatography of an enzyme, a biospecific extracting agent is employed which comprises an insoluble solid support material having covalently coupled to its surface an affinity ligand having biospecificity for the particular enzyme, so that the enzyme becomes preferentially adsorbed or bound to the extracting agent by specific interaction of the enzyme with the ligand. The affinity ligand is typically a competitive inhibitor for the particular enzyme, i.e., a material which interacts with the enzyme to form a complex therewith and temporarily inhibit the enzymatic activity thereof. The principle drawback up to now to the successful use of affinity chromatography techniques in the extraction and purification of plasminogen activating enzymes from their biological sources has been the fact that the previously known competitive inhibitors for plasminogen activating enzymes have all been relatively weak competitive inhibitors lacking sufficient affinity and specificity to the plasminogen activating enzymes to make them suitable for use as biospecific affinity chromatography ligands.

SUMMARY OF THE INVENTION

It is, therefore, a primary object of this invention to provide a procedure for the extraction and purification of plasminogen activating enzymes from their biological sources which is much simplified and more efficient as compared with the cumbersome, multi-step procedures previously employed for this purpose.

Another object of this invention is to provide an improved procedure for the extraction and purification of plasminogen activating enzymes from their biological sources employing affinity chromatography techniques.

A further object of this invention is to provide a biospecific extracting agent which is highly effective for the extraction and purification of plasminogen activating enzymes from crude preparations thereof by affinity chromatography techniques.

Still another object of this invention is to provide novel competitive inhibitors for plasminogen activating enzymes which have a higher degree of affinity and specificity to plasminogen activating enzymes as compared with the previously known competitive inhibitors for such enzymes.

A still further object of this invention is to provide novel competitive inhibitors in accordance with the preceding object, whose affinity and specificity to plasminogen activating enzymes are sufficiently great so as to make them suitable for use as biospecific affinity chromatography ligands in the extraction and purification of plasminogen activating enzymes from crude preparations thereof.

Yet another object of this invention is to provide a method whereby the competitive inhibitor ligands in accordance with the preceding object can be effectiveloy covalently coupled to the surface of an insoluble solid support material so as to provide a highly effective and efficient biospecific extracting agent for the extraction and purification of plasminogen activating enzymes from crude preparations thereof by affinity chromatography techniques.

The above and other objects are achieved in accordance with the present invention by providing a novel plasminogen activating enzyme-specific competitive inhibitor consisting of an amino-terminated α-N-substituted aminocarboxylic acid or the acid derivatives thereof, said aminocarboxylic acid having the formula:

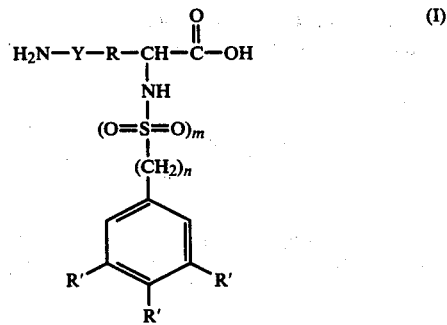

wherein R is a bivalent $C_1$–$C_4$ saturated aliphatic hydrocarbon radical, Y is selected from the group consisting of phenylene and a bivalent $C_2$–$C_6$ unsaturated aliphatic hydrocarbon radical, R and Y together containing from 6 to 10 carbon atoms, each R' is the same or different member selected from the group consisting of hydrogen, methyl and ethyl, m is 0 or 1, and n is 0, 1 or 2.

The competitive inhibitors as defined by the above formula have a sufficiently high degree of affinity and specificity to plasminogen activating enzymes so as to make them suitable for use as biospecific affinity chromatography ligands. When covalently coupled to the surface of a water-insoluble solid support material through a spacer chain of at least 4 carbon atoms, such competitive inhibitor ligands are effective as biospecific extracting agents for use in affinity chromatography of plasminogen activating enzymes, such as urokinase, cytokinase, and the like, from crude aqueous preparations thereof, such as mammalian urine, mammalian body tissue preparations, mammalian plasma and spent tissue culture growth medium. In preparing the biospecific extracting agent in accordance with the present invention, a preliminary ligand having a terminal nitro group in place of the terminal amino group of the competitive inhibitor ligand, is first covalently coupled to the support structure, and thereafter such terminal nitro group is reduced to an amino group to thereby convert the preliminary ligand to the competitive inhibitor ligand.

The biospecific extracting agent so produced is used for the extraction and purification of plasminogen activating enzymes from crude aqueous preparations thereof in accordance with the affinity chromatography method of the present invention, by first contacting the crude aqueous preparation with the biospecific extracting agent, whereby the plasminogen activating enzyme becomes preferentially adsorbed or bound to the extracting agent by specific interaction of the plasminogen activating enzyme with the ligand moiety of the extracting agent. The extracting agent is then washed with an aqueous washing agent which is a non-eluant for the plasminogen activating enzyme so as to remove from the extracting agent extraneous material remaining from the crude preparation. The plasminogen activating enzyme is thereafter eluted from the extracting agent. This procedure results in a 350 to 700 fold increase in the specific activity or purity of the plasminogen activating enzyme and also serves to concentrate the enzyme. Normally, 90 to 100% recovery of the plasminogen activating enzyme is possible using this procedure.

DESCRIPTION OF PREFERRED EMBODIMENT

The competitive inhibitor ligands in accordance with the present invention may be readily synthesized using the Schotten-Baumann procedure, wherein a nitro-terminated α-aminocarboxylic acid having the formula:

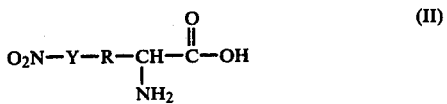

wherein R and Y are as defined above, is reacted in a basic medium with an aryl chloride having the formula:

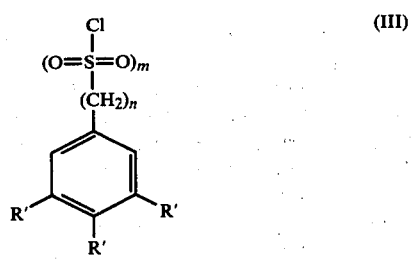

wherein R′, m and n are as defined above, to form a nitroterminated α-N-substituted aminocarboxylic acid having the formula:

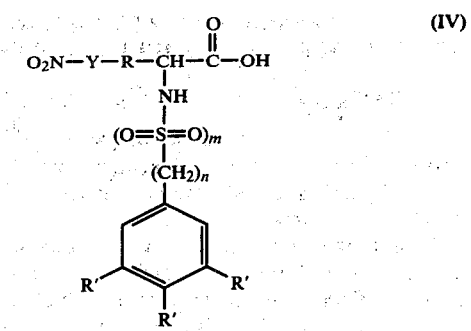

wherein R, Y, R′, m and n are as defined above. The nitroterminated α-N-substituted aminocarboxylic acid, which is utilized as the preliminary ligand in the preparation of the biospecific extracting agent in accordance with the present invention as described in more detail hereinafter, is then chemically reduced by methods well known in the art to the amino-terminated α-N-substituted aminocarboxylic acid of Formula (I), above, to form the competitive inhibitor ligand of the present invention.

For example, α-N-benzylsulfonyl-p-aminophenylalanine, the preferred competitive inhibitor ligand in accordance with the present invention, may be synthesized by reacting one equivalent of p-nitrophenylalanine dissolved in 0.9 to 1.7 equivalents of sodium hydroxide, with 0.5 to 4.0 equivalents of benzylsulfonyl chloride dissolved in 0.6 to 6 equivalents of sodium hydroxide, filtering the insoluble by-products, and acidifying the solution to a pH of 3 to 5 to produce a fine precipitate of α-N-benzylsulfonyl-p-nitrophenylalanine. Chemical reduction of the nitro group of this latter compound with, for example, a 0.1 M sodium dithionite aqueous solution, results in the formation of the competitive inhibitor ligand, α-N-benzylsulfonyl-p-aminophenylalanine. A similar procedure may be employed for synthesizing the other competitive inhibitor ligands encompassed by Formula (I), above. Although these competitive inhibitors are preferably used in the carboxylic acid form represented by Formula (I), it will be understood that the common acid derivatives thereof, e.g., wherein the OH group is replaced by Cl, Br, I, $NH_2$, SH, etc., are likewise effective.

The competitive inhibitors encompassed by Formula (I), above, and their common acid derivatives, are water-soluble compounds having a high degree of affinity and specificity to plasminogen activating enzymes, and can be used in various applications wherein suppression of plasminogen activator activity is desired, for example, in various assays. Furthermore, they can be used in aqueous solution as an eluting agent for the plasminogen activating enzymes in the affinity chromatography procedure of the present invention, as described in more detail hereinafter. As pointed out above, the preferred competitive inhibitor in accordance with the present invention is α-N-benzylsulfonyl-p-aminophenylalanine, which is the compound of Formula (I), above, wherein R is methylene, Y is phenylene, each R′ is hydrogen, m is 1, and n is 1.

Biospecific extracting agents for use in the affinity chromatography procedure in accordance with the present invention, are obtained by insolubilizing the above-described competitive inhibitor ligands by covalent coupling to a water-insoluble solid support material. Although agaroses such as, for example, Sepharose or Bio-Gel A, are the preferred support materials for use in the present invention, any other suitable support material commonly employed in affinity chromatography procedures may be used in preparing the biospecific extracting agents of the present invention. Typical support materials include cross-linked dextrans such as Sephadex, cross-linked polyacrylamides such as Bio-Gel P, agaropectin, collagen, glass, silica clays, cellulose and cellulose derivatives, and the like. These support materials are characteristically insoluble in aqueous solutions and preferably have low hydrophobicity and a non-ionic character.

The competitive inhibitor ligand is covalently coupled to the surface of the support material through a spacer chain of at least 4 carbon atoms. The spacer chain is necessary in order to ensure that the ligand is sufficiently distant from the support surface to minimize steric interference. Any of the spacer chains commonly employed in preparing affinity chromatography materials can be employed in preparing the biospecific extracting agent in accordance with the present invention. Typical spacer chains include, for example, epsilon-aminocaproic acid, 1,6-hexanediamine, beta-alanine, bis(3-aminopropyl) amine, glycine, glycyl glycine, succinamidoethylamine, succinamidobutylamine, succinamidohexamethylamine, and the like. A preferred spacer chain in accordance with the present invention comprises the amino-terminated diamido reaction product of 2 molecules of 1,6-hexanediamine with 1 molecule of succinic anhydride.

In preparing the biospecific extracting agent in accordance with the present invention, the spacer chain is preferably first covalently coupled to the surface of the support material, the spacer chain being terminally reactive at its free end with a carboxyl group or acid derivative thereof. Any of the coupling procedures well known in the art, such as the cyanogen bromide method, the bisoxirane method, or the divinylsulfone method (all fully described in "Methods in Enzymology," Volume 34 B, Academic Press, 1974, pages 21 to 29), can be used for covalently coupling the spacer chain to the support surface, depending upon the particular support and spacer chain employed. In a preferred embodiment of the present invention, an agarose support is employed, and the surface thereof is first activated by reaction thereof with cyanogen bromide, and the activated surface is then reacted sequentially with 1,6-hexanediamine, succinic anhydride, and 1,6-hexanediamine to thereby form a spacer chain covalently coupled at one end to the agarose support surface and terminating at its free end in a free amino group.

To the free end of the spacer chain is then covalently coupled a preliminary ligand moiety having the formula:

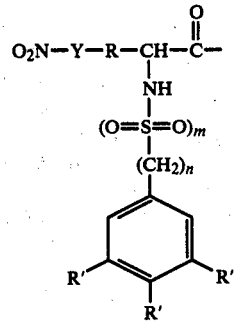

(V)

wherein R, Y, R′, m and n are as defined above. The covalent coupling of the preliminary ligand moiety to the spacer chain is effected by reacting the terminally reactive free end of the spacer chain with the nitro-terminated α-N-substituted aminocarboxylic acid of Formula (IV), above, or an acid derivative thereof. In the preferred embodiment of the invention, the spacer chain terminates in a free amino group, and this free amino group is reacted with the carboxylic acid of the preliminary ligand moiety, e.g., α-N-benzylsulfonyl-p-aminophenylalanine, to form an amido linkage.

After the preliminary ligand moiety has been covalently coupled to the spacer chain, the terminal nitro group of the preliminary ligand moiety is chemically reduced to an amino group in the same manner as described above in the preparation of the free competitive inhibitor ligand. Thus, while any of the methods well known in the art for reducing nitro compounds to primary amino compounds may be used, the preferred method is reduction with sodium dithionite aqueous solution. The preliminary ligand moiety is thereby converted to a plasminogen activating enzyme-specific competitive inhibitor ligand moiety having the formula:

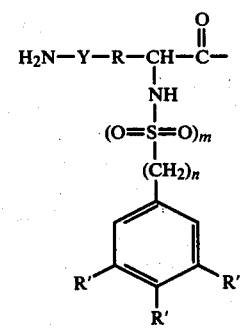

(VI)

wherein R, Y, R′, m and n are as defined above.

In order to optimize the specificity to plasminogen activating enzymes of the biospecific extracting agent of the present invention, the extracting agent should not have a net positive charge. Since any unreacted primary amino groups on the support material or on the spacer chain would contribute to the extracting material having a net positive charge, it is preferred that all of such amino groups be blocked. This is preferably accomplished by acylation of such unreacted amino groups with an aliphatic carboxylic acid anhydride, such as acetic anhydride, after the preliminary ligand moiety has been covalently coupled to the support structure and prior to the step of converting the preliminary ligand moiety to the competitive inhibitor ligand moiety.

The biospecific extracting agent prepared in the manner described above has a high degree of affinity and specificity to plasminogen activating enzymes, and can be used in the form of either a packed column or a slurry in the extraction and purification of such enzymes from crude aqueous preparations thereof by affinity chromatography. Thus, by means of the biospecific extracting agent and affinity chromatography procedure of the present invention, urokinase may be extracted and purified from mammalian urine, cytokinase may be extracted and purified from a crude aqueous preparation of mammalian body tissue, plasma plasminogen activator may be extracted and purified from plasma, and the plasminogen activator present in spent tissue culture growth medium can be extracted and purified therefrom. In all of these cases, when the crude aqueous preparation is contacted with the biospecific extracting agent of the present invention, the plasminogen activating enzyme becomes preferentially adsorbed or bound to the extracting agent by specific interaction of the plasminogen activating enzyme with the competitive inhibitor ligand moiety thereof. The extracting agent is thereafter washed with an aqueous washing agent which is a non-eluant for the plasminogen activating enzyme, such as a dilute aqueous sodium phosphate buffer at a pH in the approximate range of 5.0 to 9.0, so as to remove from the extracting agent extraneous material remaining from the crude preparation. The plasminogen activating enzyme is thereafter eluted from the extracting agent by any one of several elution techniques. For example, the elution may be by ionic strength perturbation effected by washing the extracting agent with a high ionic strength aqueous solution, such as 8% sodium chloride or potassium chloride in a dilute aqueous sodium phosphate buffer at a pH of about 7. The elution may also be by pH change effected by washing the extracting agent with an acidic aqueous solution having a pH of less than about 5 or with a basic aqueous solution having a pH of greater than about 9. Another alternative elution technique is by washing the extracting agent with an aqueous solution of a soluble substrate for the plasminogen activating enzyme, such as α-benzoyl-L-arginine amide; or an aqueous solution of a soluble competitive inhibitor for the plasminogen activating enzyme, such as α-N-benzylsulfonyl-p-aminophenylalanine or any of the other competitive inhibitors of the present invention encompassed by Formula (I) above. Other elution techniques include treatment with denaturing agents, such as urea or guanidine, or by temperature increase.

When the biospecific extracting agent and affinity chromatography procedure of the present invention is employed in extracting and purifying the plasminogen activating enzyme from spent tissue culture growth medium, an undesirable amount of non-specific binding of extraneous protein to the extracting agent may occur, due to the presence of bovine serum albumin which is a component of the tissue culture growth medium. In order to decrease the amount of such non-specific binding to the extracting agent, a small amount, e.g., 0.1%, of an anionic or neutral detergent is preferably added to the spent tissue culture growth medium prior to its being contacted with the extracting agent. A suitable neutral detergent is Triton X-100 (a mixture of various polyoxyethylene ethers). Examples of suitable anionic detergents are Tween 20 (polyoxyethylene sorbitan monolaurate), Tween 40 (polyoxyethylene sorbitan monopalmitate), Tween 60 (polyoxyethylene sorbitan monostearate), Tween 80 (polyoxyethylene sorbitan monooleate), and Tween 85 (polyoxyethylene sorbitan trioleate). Alternatively, the spent tissue culture growth medium, prior to its being contacted with the extracting agent of the present invention, may be pretreated for specific removal therefrom of bovine serum albumin by methods known in the art, for example, by passage through an oleic acid-Sepharose affinity column, in accordance with the method of Peters et al, J. Biol. Chem. 248:2447, 1973.

The following examples are given for the purpose of illustrating preferred embodiments of the invention.

EXAMPLE 1

The synthesis of α-N-benzylsulfonyl-p-nitrophenylalanine was carried out as follows using the Schotten-Baumann procedure. 20 m moles (1 equivalent) of p-nitro phenylalanine was dissolved in 1.2 equivalents of 1N NaOH while the solution was vigorously stirred and cooled in an ice bath. 1.2 equivalents of benzylsulfonyl chloride in 1.4 equivalents of 1N NaOH was then added to the cooled p-nitrophenylalanine solution in 5 equal portions at 15 to 20 minute intervals. The reaction mixture was stirred at room temperature for 1 hour and then made basic to litmus paper with 1N NaOH. The insoluble by-products were separated by vacuum filtration and the filtrate washed with two 20 Ml portions of ether. After removal of the ether layer, the solution was acidified to Congo red (pH 3 to 5), using concentrated HCl, which produced a fine precipitate of α-N-benzylsulfonyl-p-nitrophenylalanine, which was recrystallized by acidification of a dilute alkaline solution thereof. The melting point of the product was 187° C.

EXAMPLE 2

The plasminogen activating enzyme-specific competitive inhibitor α-N-benzylsulfonyl-p-aminophenylalanine was prepared by treating the α-N-benzylsulfonyl-p-nitrophenylalanine prepared in accordance with Example 1, with a 0.1 M sodium dithionite aqueous solution for 30 minutes, thereby reducing the aromatic nitro group to the aryl amine.

EXAMPLE 3

A biospecific extracting agent was prepared as follows. 100 ml of dry Sepharose-4B was washed with 3 liters of distilled water. The imino carbonate derivative of Sepharose-4B was prepared by reaction of 30 g of finely ground cyanogen bromide (CNBr) with a 100 ml aqueous suspension of the gel, at 4° C., in a well ventilated hood. Immediately after addition of the CNBr, the pH of the reaction mixtue was raised to pH 11.0 by addition of 10N NaOH and sufficient ice was added to maintain the temperature below 10° C. during the reaction. The reaction was allowed to proceed for 15 minutes until stabilization of the pH occurred (Cuatrecasas J. Biol. Chem. 245,3059, 1970). The reaction mixture was then rapidly filtered and the activated Sepharose washed with 1 liter of cold distilled water.

The activated Sepharose was then suspended in 50 ml of a previously prepared, precooled 0.2 M 1,6-hexanediamine solution adjusted to pH 10 with 5 and the reaction allowed to proceed at 4° C. for 12 hours.

50 ml of distilled water was added to 50 ml of the washed 6-aminohexyl-Sepharose-4B and the pH lowered to 8.0 with 1N NaCl. Succinic anhydride (5.0 g) was added to the reaction mixture at 4° C. and the pH maintained at 8.0 using 10N NaOH. After 30 minutes the reaction mixture was filtered and washed.

The matrix material was then suspended in 50 Ml distilled water containing 5 ml of 1,6-hexanediamine, and the pH of the mixture was adjusted to 5.0 with concentrated HCl. Sufficient crystalline [3-(dimethylamino)-propyl)-] ethyl carbodiimide HCl was added as a catalyst to the suspension so that the final concentration of the carbodiimide was 3 mM. The reaction was allowed to proceed at room temperature for 3 hours, maintaining the reaction mixture at pH 5.0 with 1N NaOH, after which the modified Sepharose-4B was filtered and washed.

A 5 ml aqueous solution containing 0.04 moles of the α-N-benzylsulfonyl-p-nitrophenylalanine prepared in accordance with Example 1, was added to 25 ml of the previously washed, modified Sepharose-4B material suspended in 25 ml distilled water. The pH was adjusted to 5.0 after which sufficient [3-dimethylaminopropyl] ethyl carbodiimide HCl was added as a catalyst to the reaction mixture to make the final concentration of the carbodiimide 3 mM. The reaction was allowed to proceed at room temperature for 3 hours while maintaining the pH constant at 5.0 with 1N NaOH. The resulting gel, consisting of the α-N-benzylsulfonyl-p-nitrophenylalanine covalently coupled to the Sepharose-4B, was then filtered and washed.

To 25 ml of the resulting gel in 25 ml of saturated sodium acetate was added, at 4° C., 20 ml of acetic anhydride. The reaction was allowed to proceed for 30 minutes, at 4° C., after which the gel was filtered and washed.

The gel was then suspended in a 0.1 M sodium dithionite aqueous solution for 30 minutes, thereby reducing the aromatic nitro group to the aryl amine, and resulting in α-N-benzylsulfonyl-p-aminophenylalanine covalently coupled to Sepharose-4B. After washing, the resulting gel was stored at 4° C. in 0.1 M sodium phosphate buffer, pH 7.0, containing $10^{-3}$ M sodium azide as a bactericidal agent.

EXAMPLE 4

The biospecific extracting agent prepared in accordance with Example 3, was used in the extraction and purification of urokinase from human urine by affinity chromatography, as follows. A sample of human urine, having a urokinase activity of 100 CTA/mg, was passed through a packed column of the biospecific extracting agent prepared in accordance with Example 3. The extracting agent was then washed with 100 mls of 0.05 M sodium phosphate buffer, pH 7.0, which resulted in a washing out of protein and other extraneous chemical material containing no urokinase activity. The extracting agent was then washed with 8% NaCl in 0.05 M sodium phosphate buffer, pH 7.0, and a protein fraction containing urokinase in a concentrated, purified form, having a urokinase activity of 35,000 CTA/mg, was recovered at between 90% and 100% yield.

What is claimed is:

1. A plasminogen activating enzyme-specific competitive inhibitor selected from the group consisting of α-N-benzylsulfonyl-p-aminophenylalanine and its acid derivatives in which the hydroxyl group of its carboxyl group has been replaced by a substituent hydrolyzable to said hydroxyl group.

2. A biospecific extracting agent for use in affinity chromatography of plasminogen activating enzymes from crude aqueous preparations thereof, comprising a water-insoluble solid support material having covalently coupled to the surface thereof through a spacer chain of at least 4 carbon atoms a ligand which is the plasminogen activating enzyme-specific competitive inhibitor of claim 1, said ligand after being coupled to said support material having the formula:

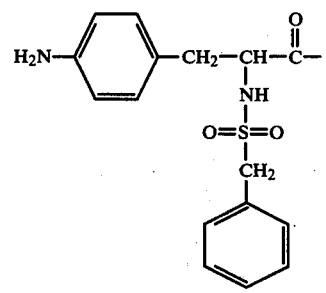

3. The extracting agent of claim 2, wherein said support material is agarose.

4. The extracting agent of claim 3, wherein said spacer chain comprises the amino-terminated diamido reaction product of 2 molecules of 1,6-hexandiamine with 1 molecule of succinic anhydride, and said ligand is covalently coupled to said spacer chain by an amido linkage between the carbonyl group of said ligand and the terminal amino group of said spacer chain.

5. The extracting agent of claim 4, wherein all unreacted amino groups thereon other than the terminal amino group of said ligand have been blocked by acylation.

6. A method of preparing a biospecific extracting agent for use in affinity chromatography of plasminogen activating enzymes from crude aqueous preparations thereof, comprising the steps of:

(a) covalently coupling to the surface of a water-insoluble solid support material through a spacer chain of at least 4 carbon atoms a preliminary ligand moiety which after being coupled to said support material has the formula:

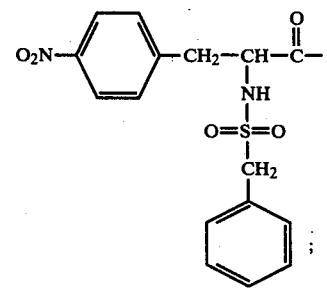

and (b) thereafter reducing the terminal nitro group of said preliminary ligand moiety to an amino group, thereby converting said preliminary ligand moiety to a plasminogen activating enzyme-specific competitive inhibitor ligand moiety.

7. The method of claim 6, wherein the covalent coupling of said preliminary ligand moiety to the surface of said support material is effected by first covalently coupling said spacer chain to the surface of said support material, said spacer chain being terminally reactive at its free end with a carboxyl group, and thereafter reacting said terminally reactive free end of said spacer chain with α-N-benzylsulfonyl-p-nitrophenylalanine.

8. The method of claim 7, wherein said free end of said spacer chain terminates in a free amino group.

9. The method of claim 8, including the further step, prior to step (b), of blocking any unreacted amino groups on the product resulting from step (a) by acylation thereof with an aliphatic carboxylic acid anhydride.

10. The method of claim 6, wherein said reduction of said terminal nitro group of said preliminary ligand moiety to an amino group is effected with sodium dithionite.

11. The method of claim 6, wherein said support material is agarose, and the covalent coupling of said preliminary ligand moiety to the surface of said agarose support is effected by first activating said surface by reaction thereof with cyanogen bromide, reacting said activated surface sequentially with 1,6-hexanediamine, succinic anhydride, and 1,6-hexanediamine to thereby form said spacer chain terminating in a free amino group, and thereafter reacting said free amino group with α-N-benzylsulfonyl-p-nitrophenylalanine.

12. The method of claim 11, including the further step, prior to step (b), of blocking any unreacted amino groups on the product resulting from step (a) by acylation thereof with an aliphatic carboxylic acid anhydride.

13. The method of claim 12, wherein said aliphatic carboxylic acid anhydride is acetic anhydride.

14. An affinity chromatography method for the extraction and purification of plasminogen activating enzymes from crude aqueous preparations thereof, comprising the steps of:

(a) contacting a crude aqueous preparation of a plasminogen activating enzyme with a biospecific extracting agent comprising a water-insoluble solid support material having covalently coupled to the surface thereof through a spacer chain of at least 4 carbon atoms a ligand which is the plasminogen activating enzyme-specific competitive inhibitor of claim 1, said ligand after being coupled to said support material having the formula:

$$H_2N-\underset{}{\bigcirc}-CH_2-CH(NH-S(=O)_2-CH_2-\bigcirc)-C(=O)-$$

whereby said plasminogen activating enzyme becomes preferentially bound to said extracting agent by specific interaction of said plasminogen activating enzyme with said ligand;

(b) washing said extracting agent with an aqueous washing agent which is a non-eluant for said plasminogen activating enzyme so as to remove from said extracting agent extraneous material remaining from said crude preparation; and (c) eluting said plasminogen activating enzyme from said extracting agent.

15. The method of claim 14, wherein said support material is agarose, said spacer chain comprises the amino-terminated diamido reaction product of 2 molecules of 1,6-hexanediamine with 1 molecule of succinic anhydride, and said ligand is covalently coupled to said spacer chain by an amido linkage between the carbonyl group of said ligand and the terminal amino group of said spacer chain.

16. The method of claim 15, wherein all unreacted amino groups on said extracting agent other than the terminal amino group of said ligand have been blocked by acylation.

17. The method of claim 14, wherein said washing agent is a dilute aqueous sodium phosphate buffer at a pH in the approximate range of 5.0 to 9.0.

18. The method of claim 15, wherein the elution of said plasminogen activating enzyme from said extracting agent is by ionic strength perturbation effected by washing said extracting agent with a high ionic strength aqueous solution.

19. The method of claim 18, wherein said high ionic strength aqueous solution is about 8% sodium chloride in a dilute aqueous sodium phosphate buffer at a pH of about 7.

20. The method of claim 14, wherein the elution of said plasminogen activating enzyme from said extracting agent is by pH change effected by washing said extracting agent with an acidic aqueous solution having a pH of less than about 5 or with a basic aqueous solution having a pH of greater than about 9.

21. The method of claim 14, wherein the elution of said plasminogen activating enzyme from said extracting agent is effected by washing said extracting agent with an aqueous solution of a soluble competitive inhibitor or substrate for said plasminogen activating enzyme.

22. The method of claim 21, wherein the elution of said plasminogen activating enzyme from said extracting agent is effected by washing said extracting agent with an aqueous solution of α-N-benzylsulfonyl-p-amino phenylalanine.

23. The method of claim 14, wherein said crude preparation is mammalian urine, and said plasminogen activating enzyme extracted therefrom is urokinase.

24. The method of claim 14, wherein said crude preparation is prepared from mammalian body tissue, and said plasminogen activating enzyme extracted therefrom is cytokinase.

25. The method of claim 14, wherein said crude preparation is mammalian plasma.

26. The method of claim 14, wherein said crude preparation is spent tissue culture growth medium, and an anionic or neutral detergent is added thereto prior to its being contacted with said extracting agent in order to decrease the amount of nonspecific binding to said extracting agent.

27. The method of claim 26, wherein said detergent is selected from the group consisting of polyoxyethylene ethers, polyoxyethylene sorbitan monolaurate, polyoxyethylene sorbitan monopalmitate, polyoxyethylene sorbitan monostearate, polyoxyethylene sorbitan monooleate and polyoxyethylene sorbitan triolate.

28. The method of claim 14, wherein said crude preparation is spent tissue culture growth medium which has been pretreated for specific removal therefrom of bovine serum albumin.

* * * * *